United States Patent [19]

Krenitsky

[11] Patent Number: 5,061,708

[45] Date of Patent: Oct. 29, 1991

[54] THERAPEUTIC GUANINE ESTERS

[75] Inventor: Thomas A. Krenitsky, Chapel Hill, N.C.

[73] Assignee: Burroughs Wellcome Co., Research Triangle Park, N.C.

[21] Appl. No.: 442,415

[22] Filed: Nov. 21, 1989

Related U.S. Application Data

[63] Continuation of Ser. No. 228,387, Aug. 4, 1988, abandoned.

[30] Foreign Application Priority Data

Nov. 5, 1987 [GB] United Kingdom ............... 8725939

[51] Int. Cl.$^5$ ................... A61K 31/52; C07D 473/18
[52] U.S. Cl. ................................. 514/262; 544/276
[58] Field of Search .................... 544/276; 514/262

[56] References Cited

U.S. PATENT DOCUMENTS

| 4,199,574 | 4/1980 | Schaeffer | 544/276 X |
| 4,287,188 | 9/1981 | Schaeffer | 544/244 X |
| 4,294,831 | 10/1981 | Schaeffer | 544/277 X |
| 4,457,919 | 7/1984 | Simon et al. | 514/262 |
| 4,544,634 | 10/1985 | Krenitsky | 514/261 X |
| 4,548,819 | 10/1985 | De Clercq et al. | 544/277 |
| 4,567,182 | 1/1986 | Ferraris | 514/262 |
| 4,695,570 | 9/1987 | Krenitsky | 514/261 |
| 4,745,119 | 5/1988 | Krenitsky | 514/262 |
| 4,957,924 | 9/1990 | Beauchamp | 514/262 |

FOREIGN PATENT DOCUMENTS

| 0099493 | 2/1984 | European Pat. Off. . |
| 1561380 | 2/1980 | United Kingdom . |

OTHER PUBLICATIONS

Colla et al., J. Med. Chem., vol. 26, No. 4, pp. 602–604 (04/83).

*Primary Examiner*—Diana G. Rivers
*Attorney, Agent, or Firm*—Donald Brown; Lawrence A. Nielsen; Hannah O. Green

[57] ABSTRACT

The present invention relates to certain amino acid esters of the purine nucleoside acyclovir, pharmaceutically acceptable salts thereof and their use in the treatment and prophylaxis of herpes virus infections. The invention also includes pharmaceutical formulations and processes for the preparation of such compounds.

18 Claims, No Drawings

THERAPEUTIC GUANINE ESTERS

This is a continuation of copending application Ser. No. 07/228,387 filed on Aug. 4, 1988 now abandoned.

The invention relates to new esters of 9-(2-hydroxyethoxymethyl)guanine having valuable antiviral properties.

9-(2-Hydroxyethoxymethyl)guanine, otherwise known as acyclovir, possesses a potent antiviral activity, particularly against herpes viruses (H. J. Schaeffer et al, "Nature", 272 583–585 (1978), UK Patent Specification 1523865 and U.S. Pat. No. 4,199,574). Acyclovir is however only poorly soluble in water, thereby limiting the formulation of the drug in aqueous pharmaceutical preparations where solubility is required.

Also acyclovir is only poorly absorbed from the gastrointestinal tract after oral administration (15% recovery in the urine when tested in rats and 20% in humans). Such low bioavailability requires the administration of large doses of drug in order to achieve and maintain effective anti-viral levels in the plasma.

European Patent Specification 99493 describes amino acid esters of acyclovir, specifically the glycine and alanine esters which show improved water-solubility compared with acyclovir.

I have now discovered that the isoleucine esters of acyclovir, characterised by side-chain branching adjacent to the α-carbon atom, and which were not disclosed in European Patent Specification 99493, surprisingly have improved bioavailability after oral administration compared with the alanine and glycine esters mentioned therein.

According to one feature of the present invention I provide the compounds of formula (I)

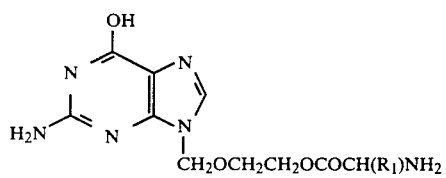

wherein $R_1$ represents a group of formula $-CH[CH_3]CH_2CH_3$ and pharmaceutically acceptable salts thereof. The compound of formula (I) wherein the group of formula $-CH[CH_3]CH_2CH_3$ is in the L-configuration can also be named 2-(2-amino-1,6-dihydro-6-oxo-9H(purin-9-yl)methoxy)ethyl L-isoleucinate. The isoleucine moieties may be in the D, L, or racemic DL configuration but preferably in the L-form.

In tests in rats, measuring the urinary recovery as acyclovir (% dose administered) after oral administration, the compounds of the invention show a large increase in absorption from the gut compared with the other esters and compared with acyclovir. This enables less drug to be administered while still providing equivalent drug levels in the plasma after oral absorption.

In addition to the relatively high bioavailability, the compounds according to the invention possess substantially the same antiviral effect as acyclovir in vitro. The advantageous increase in bioavailability of the compound is thus not gained at the expense of antiviral potency. Indeed, it has been found that in certain clinical applications, e.g., the treatment of stromal keratitis, certain amino acid esters have been found to provide a superior therapeutic effect to acyclovir (EP 99493).

The pharmaceutically acceptable salts of the compounds of formula (I) are preferably acid addition salts derived from an appropriate acid, e.g. hydrochloric, sulphuric, phosphoric, maleic, fumaric, citric, tartaric, lactic, acetic or p-toluenesulphonic acid. Particularly preferred salts are the hydrochloride salts of compounds of formula (I).

In experiments in animals, it was discovered that the oral administration of the compounds of formula (I) above produced measurable levels of acyclovir in the plasma. Thus according to another aspect of the invention I provide a means of generating acyclovir in vivo by administration of a compound of formula (I) above or a pharmaceutically acceptable salt thereof to a mammal.

The compounds according to the invention may be prepared in conventional manner, e.g., by a process as described below.

Thus, according to a further feature of the present invention I provide a process for the preparation of the compounds of formula (I) above and pharmaceutically acceptable salts thereof which comprises a) reacting a compound of formula (II)

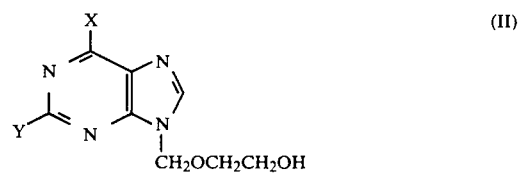

wherein X is an optionally protected hydroxy group, and Y is an optionally protected amino group with an optionally protected isoleucine or a functional equivalent thereof;

b) converting a compound of formula (III)

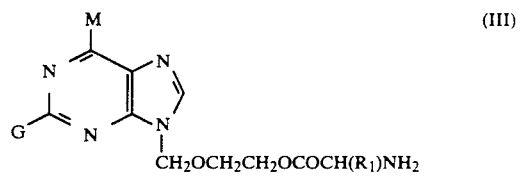

(wherein $R_1$ is as defined above; and M represents a hydroxy group and G represents an atom or group that can be replaced by or converted to an amino group; or G represents an amino group and M represents an atom or group that can be replaced by or converted to a hydroxy group) into a compound of formula (I) or a pharmaceutically acceptable salt thereof; or c) reacting a compound of formula (IV)

(wherein X and Y are as defined above and Q represents a leaving atom or group) with a compound of formula (V)

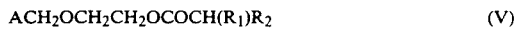

$ACH_2OCH_2CH_2OCOCH(R_1)R_2$  (V)

(wherein $R_1$ is as defined above, A represents a leaving group or atom and $R^2$ is an optionally protected amino group); and optionally effecting one or more of the following conversions;

i) removal of any protecting groups;
  ii) where the resulting product is a compound of formula (I), conversion of the said compound into a pharmaceutically acceptable salt thereof; and
  iii) where the resulting product is a pharmaceutically acceptable salt of a compound of formula (I), conversion of the said salt into the parent compound.

With regard to process a), the esterification reaction may be carried out in conventional manner, for example in a solvent such as pyridine or dimethylformamide in the presence of a coupling agent such as N,N'-dicyclohexylcarbodiimide, optionally in the presence of a catalytic base such as 4-dimethylaminopyridine. The water formed during the reaction may, if desired, be removed in conventional manner, for example by distillation or by the addition of a water-binding substance. Subsequently, the ester obtained as reaction product may be isolated in conventional manner.

As an alternative to the use of isoleucine per se, a functional equivalent of the acid may be employed, e.g., an acid halide such as the acid cloride, or an acid anhydride. In such a case in order to avoid undesirable side-reactions, it is advantageous to use an amino-protected derivative. Examples of preferred amino-protecting groups including acyl, e.g., $C_{1-4}$ alkanoyl such as acetyl and aryloxycarbonyl, e.g., benzyloxy carbonyl. A suitable amino-protected derivative, for example, is one wherein the amino group of the amino acid is replaced by an azido group.

Conversion of a compound of formula (III) into a compound of formula (I), by method b), can be achieved by various means. For example G may represent an azide group which can be reduced to an amino group by catalytic hydrogenation, using a suitable catalyst such as palladium on carbon. Alternatively, G may each represent a halogen atom or an alkylthio or alkylsulphonyl group which can be converted to an azide group which in turn can be converted to an amino group by catalytic hydrogenation using, for example, hydrogen in the presence of palladium on carbon. For the preparation of the compound of formula (I), a compound of formula (III) wherein M is an amino group may be converted to a hydroxy group for example by treatment with a deaminating enzyme such as adenosine deaminase.

These processes together with other conventional processes are described in Fused Pyrimidines, Part II, Purines, Ed. by D. J. Brown (1971), Wiley-Interscience.

In process (c), the group Q in formula (IV) may, for example, represent a hydrogen atom; an acyl group, e.g., a $C_{1-4}$ alkanoyl group such as an acetyl group or an aroyl group such an a benzoyl group; or a tri-$C_{1-4}$ alkylsilyl group such as a trimethylsilyl group. The group A in formula (V) may, for example, represent a halogen atom (e.g. chlorine) or an acyloxy group wherein the acyl moiety may be, for example, a $C_{1-4}$ alkanoyl group such as acetyl or an aroyl group such as benzoyl. The group $R^2$ may represent an amino-protecting group such as for example, $C_{1-4}$ alkanoyl (e.g., acetyl) or aryloxycarbanoyl (e.g., benzyloxycarbonyl) it may also represent an azido group. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (IV) and (V) in the presence of a catalytic amount of a strong acid, e.g., sulphuric acid.

Compounds of formulae (II) to (V), employed as intermediates in the synthesis of the compound of formula (I), can be prepared in conventional manner, e.g., by procedures described in U.K. Patent Specification No. 1523865. These methods rely on intermediates prepared from simply substituted purines, which may be available commercially, or prepared according to techniques which are well known per se and which are disclosed in the literature such as the aforementioned text-book. Thus, for example, compounds of formula (III) may be generally prepared by using an analogous procedure to that of process (c), i.e., reacting an appropriate purine with a compound of formula (V).

The optional conversions i), ii) and iii) may be effected in conventional manner. Thus, for example, removal of protecting groups in conversion i) may be effected by hydrolysis, solvolysis or hydrogenolysis as appropriate. With regard to removal of protecting groups on the amino acid acyl radicals, hydrogenolysis, e.g., of aryloxycarbonyl protecting groups, and conversion of azido group, e.g., by catalytic hydrogenation, e.g., using a palladium catalyst, are preferred. With regard to protection of the groups in the 2- and/or 6-positions of purine nucleus, these may be selected for example from arylmethyl groups, e.g., benzyl; or tri-$C_{1-4}$ alkylsilyl, e.g., trimethylsilyl. Arylmethyl blocking groups, may be removed for example by hydrogenolysis, e.g., by hydrogenation in the presence of Raney nickel or a palladium catalyst. Trialkylsilyl blocking groups may be removed for example by solvolysis, e.g., by alcoholysis.

The conversion of a compound of formula (I) into a pharmaceutically acceptable salt may be effected in conventional manner, for example, by treatment of the compound with an appropriate acid to form an acid addition salt, for example, by lyophilisation of a methanolic solution of the parent ester with an acid solution.

Similarly, conversion of a salt into the parent compound of formula (I) may be effected in conventional manner.

The present invention also provides the compounds of formula (I) and pharmaceutically acceptable salts thereof (hereinafter identified as "the active compounds") for use in medical therapy, e.g., in the treatment or prophylaxis of a viral disease in an animal, e.g., a mammal such as man. The compounds are especially useful for the treatment or prophylaxis of diseases caused by various DNA viruses, such as herpes infections, for example, herpes simplex, varicella or zoster, cytomegalovirus as well as diseases caused by hepatitis B or Epstein-Barr viruses or human herpes virus -6 (HHV-6). The active compounds can also be used for the treatment or prophylaxis of retrovirus infections such as HIV infections and papilloma or wart virus infections. In addition to their use in human medical therapy, the compounds of formula (I) can be administered to other animals for treatment or prophylaxis of viral diseases, e.g., in other mammals. For example, the active compounds are especially useful for the treatment of equine rhinopneumonitis.

The present invention also provides a method for the treatment or prophylaxis of a viral disease in an animal, e.g., a mammal such as man, which comprises administering to the animal an effective antiviral amount of a compound of formula (I) or a pharmaceutically acceptable salt thereof.

The present invention also provides the use of a compound of formula (I) in the manufacture of a medicament for the treatment or prophylaxis of a viral infection.

The active compounds may be administered by any route appropriate to the condition to be treated, suitable routes including oral, rectal, nasal, topical (including buccal and sublingual) vaginal and parenteral (including subcutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. (Unless otherwise indicated, all weights of active ingredient are calculated as the parent compound of formula (I): for salts thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

The compounds of the present invention may be administered alone or in combination with other therapeutic agents, for example, with 9-(2-hydroxyethoxymethyl)guanine (acyclovir) used to treat herpes virus infections in particular HSV (I), and with zidovudine used to treat retroviral infections in particular HIV infections.

While it is possible for the active ingredients to be administered alone, it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutanous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either paraffinic or a water-miscible ointment base. Alternatively, the active ingredients may be formulated in a cream with an oil-in-water cream base. In addition topical applications may be made transdermally by means of an iontophoretic device.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e., by rapid inhalation through the nasal passage from a container of powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Formulations for intramuscular administration are particularly preferred.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

For oral administration the compositions can be in the form of a tablet, granule drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispensing agent are included. These formulations preferably contain from 15 to 85% of the active ingredient.

The following Examples illustrate the present invention.

EXAMPLE 1

2-(2-Amino-1,6-dihydro-6-oxo-9H(purin-9-yl)methoxy)ethyl L-isoleucinate hydrochloride a)
2-[(2-Amino-1,6-dihydro-6-oxo-9H-purin-9-yl)methoxy]ethyl-N[(benzyloxy)carbonyl]L-isoleucinate A mixture of acyclovir (1.0 g, 4.4. mmol; Burroughs Wellcome Co.), 4-dimethylaminopyridine (74 mg, 0.6 mmol; Aldrich Chemical Co. and Chem. Ber. 89 2921-33 [1956]), 1,3-dicyclohexylcarbodiimidide (1.6 g, 8.0 mmol; Aldrich Chemical Co. and U.S. Pat. No. 2,656,383), N-carbobenzoxy-L-isoleucine (1.8 g, 6.6 mmol; Sigma Chemical Co. and Bull. Chem. Soc. Jap (1966) 39 947 or Tetrahedron 40 (24) 5207-11 [1984]), and molecular sieves (0.3 g, Davison type 3A; Fisher Scientific, Co.) in dry N,N-dimethylformamide (80 ml) was stirred at room temperature under nitrogen. After 4 days, additional 1,3-dicyclohexylcarbodiimide (1.6 g, 8.0 mmol) and N-carbobenzoxy-L-isoleucine (1.8 g, 6.6 mmol) were added. Stirring at room temperature was continued for 7 days. The resulting mixture was filtered and the clear filtrate was concentrated in vacuo to a semi-solid residue. Elution of the residue from silica gel 60 (EM, 230-400 mesh; 8.5×14 cm) with 2.5-5% methanol/methylene chloride gave 2-[2-Amino-1,6-dihydro-6-oxo-9H-purin-9-yl)methoxy]ethyl-N-[(benzyloxy)carbonyl]-L-isoleucinate 0.8 g, 45%) as a white solid; mp 155°-157° C.

UV (MeOH): $\lambda$ max 255 nm ($\epsilon$17700), $\lambda$ sh 279 (9800), $\lambda$ min 230 (6100). NMR (200 MHz, ME$_2$SO-d$_6$): 0.73-0.80 ppm (m, 6H), 1.13-1.33 (m, 2H), 1.66-1.70 (m, 1H), 3.64 (t,2H), 3.92 (t,1H), 4.16 (m, 2H), 5.00 (s, 2H), 5.32 (s,2H) 6.47 (br s, 2H), 7.33 (s, 5H), 7.65 (d, j=8 Hz, 1H), 7.78 (s, 1H), 10.59 (br s, 1H).

MS (Cl/CH$_4$; 70° C.): m/z 473 (1.0%, M+1), 347 (23.2, M-125), 225 (100.0, M-247); $[\alpha]_d^{20°}$ C. $-3.07°$ (c 0.488, 6N HCl).

TLC: one spot on silica gel with 10% MeOH/CH$_2$Cl$_2$. R$_f$=0.38.

HPLC: one peak on Supelco LC$_8$ with 50% MeOH/H$_2$O; 100% K'=7.02.

Anal Calcd for C$_{22}$H$_{28}$N$_6$O$_6$.H$_2$O: C, 53.87; H, 6.16; N, 17.13. Found: C, 53.94; H, 6.20; N, 17.04.

b)
2-[(2-Amino-1,6-dihydro-6-oxo-9H-purin-9-yl)methoxy]ethyl L-isoleucinate hydrochloride A solution of 2-[(2-amino-1,6-dihydro-6-oxo-9H-purin-9-yl)-methoxy]-ethyl-N-[(benzyloxy)carbonyl]-L-isoleucinate (1.11 g, 2.2 mmol) in methanol-tetrahydro furan (1:1, 50 ml) was treated with 0.5N hydrochloric acid (5 ml) and 5% palladium on charcoal (0.30 g; MCB Reagents). The mixture was hydrogenated on a Parr hydrogenator at 50 psi for 11 hours, filtered through a Celite pad and the filtrate was concentrated in vacuo to give 2-[(2-amino-1,6-dihydro-6-oxo-9H-purin-9-yl)methoxy]ethyl-L-isoleucinate hydrochloride (0.86 g, 92%) as an off-white solid; mp 180°-182° C. (effervescent softening ca. 150° C.):

UV (MeOH): $\lambda$ max 254 nm ($\epsilon$13400), $\lambda$ sh 272 (9000), $\lambda$ min 224 (3600).

NMR (200 MHz, Me$_2$SO-d$_6$): 0.77-0.84 ppm (m, 6H), 1.13-1.37 (m, 2H), 1.82 (m,1H), 3.73 (t,2H), 3.87 (br t, 1H), 4.14-4.40 (m, 2H), 5.36 (s, 2H), 6.70 (br s, 2H), 7.97(s, 1H), 8.46 (br s, 3H), 10.87 (s, 1H).

MS (Cl/CH$_4$; 150° C.): m/z 367 (6.9%, M+29), 339(100, M+1), 225(92.9, M-113); $[\alpha]D^{20°}$ C. $+11.15°$ (c 2.0, HOAc).

TLC: one spot on silica gel with 10% MeOH/CH$_2$Cl$_2$ Rf=0.12; HPLC: one peak on Versapack C$_{18}$ with 10% MeOH/H$_2$O/0.1% F$_3$CCOOH;100% K'=3.74.

Anal Calcd for C$_{14}$H$_{22}$N$_6$O$_4$: 1.25 HCl. 1.10 MeOH. 0.25 H$_2$O: C, 42.81; H, 6.70; N, 19.84; Cl, 10.46. Found: C, 42.82; H, 6.50; N, 19.64; Cl, 10.46.

EXAMPLE 2

Tablet Formulations

The following formulations A, B and C are prepared by wet granulation of the ingredients with a solution of povidone, followed by addition of magnesium stearate and compression. Active ingredient is intended to mean a compound of formula (I) or a pharmaceutically acceptable salt thereof.

Formulation A

|  | mg/tablet | mg/tablet |
|---|---|---|
| Active ingredient | 250 | 250 |
| Lactose B.P. | 210 | 26 |
| Povidone B.P. | 15 | 9 |
| Sodium Starch Glycollate | 20 | 12 |
| Magnesium Stearate | 5 | 3 |
|  | 500 | 300 |

Formulation B

|  | mg/tablet | mg/tablet |
|---|---|---|
| Active ingredient | 250 | 250 |
| Lactose | 150 | — |
| Avicel PH 101 | 60 | 26 |
| Povidone B.P. | 15 | 9 |
| Sodium Starch Glycollate | 20 | 12 |
| Magnesium Stearate | 5 | 3 |
|  | 500 | 300 |

Formulation C

|  | mg/tablet |
|---|---|
| Active ingredient | 100 |
| Lactose | 200 |
| Starch | 50 |
| Povidone B.P. | 5 |
| Magnesium stearate | 4 |
|  | 359 |

The following formulations, D and E, are prepared by direct compression of the admixed ingredients. The lactose in formulation E is of the compression type.

Formulation D

|  | mg/capsule |
|---|---|
| Active Ingredient | 250 |
| Avicel | 150 |
| Magnesium Stearate | 4 |
|  | 404 |

Formulation E

|  | mg/capsule |
|---|---|
| Active Ingredient | 250 |
| Lactose | 150 |
| Avicel | 100 |
| Magnesium Stearate | 5 |
|  | 505 |

Formulation F (Controlled Release Formulation)

The formulation is prepared by wet granulation of the ingredients (below) with a solution of povidone followed by the addition of magnesium stearate and compression.

|  | mg/tablet |
|---|---|
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
|  | 700 |

EXAMPLE 3

Capsule Formulations

Formulation A

A capsule formulation is prepared by admixing the ingredients of Formulation D in Example 3 above and filling into a two-part hard gelatin capsule. Formulation B (infra) is prepared in a similar manner.

Formulation B

|  | mg/capsule |
|---|---|
| Active ingredient | 250 |
| Lactose B.P. | 143 |
| Sodium Starch Glycollate | 25 |
| Magnesium Stearate | 2 |
|  | 420 |

Formulation C

|  | mg/capsule |
|---|---|
| Active ingredient | 250 |
| Macrogol 4000 B.P. | 350 |
|  | 600 |

Capsules are prepared by melting the Macrogol 4000 BP, dispersing the active ingredient in the melt and filling the melt into a two-part hard gelatin capsule.

Formulation D

|  | mg/capsule |
|---|---|
| Active ingredient | 250 |
| Lecithin | 100 |
| Arachis Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

| | mg/capsule |
|---|---|
| Active Ingredient | 250 |
| Microcrystalline Cellulose | 125 |
| Lactose B.P. | 125 |
| Ethyl Cellulose | 13 |
| | 513 |

EXAMPLE 4

Ophthalmic Solution

| | | |
|---|---|---|
| Active ingredient | 0.5 | |
| Propylene Glycol | 0.2 | g |
| Thiomersal | 0.001 | g |
| Purified water to | 100 | ml |
| pH adjusted to 7.5 | | |

EXAMPLE 5

Injectable Formulation

| | | |
|---|---|---|
| Active Ingredient | 0.200 | g |
| Sterile, pyrogen free citrate buffer (pH 7.0) to | 10 | ml |

The active ingredient is dissolved in most of the citrate buffer (35°–40° C.), then made up to volume and filtered through a sterile micropore filter into a sterile 10 ml amber glass vial (type 1) and sealed with sterile closures and overseals.

EXAMPLE 6

Intramuscular Injection

| | | |
|---|---|---|
| Active Ingredient | 0.20 | g |
| Benzyl Alcohol | 0.10 | g |
| Glycofurol 75 | 1.45 | g |
| Water for Injection q.s. to | 3.00 | ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 7

Syrup Suspension

| | | |
|---|---|---|
| Active Ingredient | 0.25 | g |
| Sorbitol Solution | 1.50 | g |
| Glycerol | 2.00 | g |
| Sodium Benzoate | 0.005 | g |
| Flavour, | 0.0125 | ml |
| Purified Water q.s. to | 5.00 | ml |

The sodium benzoate is dissolved in a portion of the purified water and the sorbitol solution added. The active ingredient is added and dissolved. The glycerol and flavours are added and mixed in. Water is added to a final volume of 5 ml.

EXAMPLE 8

Suppository

| | mg/suppository |
|---|---|
| Active Ingredient (63 μm)* | 250 |
| Hard Fat, BP (Witepsol H15-Dynamit NoBel) | 1700 |
| | 1950 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable plastic moulds. The suppositories are allowed to cool to room temperature.

EXAMPLE 9

Pessaries

| | mg/pessary |
|---|---|
| Active ingredient 63 μm | 250 |
| Anhydrous Dextrose | 543 |
| Starch | 200 |
| Magnesium Stearate | 7 |
| | 1000 |

The above ingredients are mixed directly and pessaries prepared by direct compression of the resulting mixture.

EXAMPLE 10 a) Antiviral Activity

Herpes Simplex Virus (HSV 1) was assayed in monolayers of Vero cells in multiwell trays. Activity of compounds was determined in the plaque reduction assay, in which a cell monolayer was infected with a suspension of HSV 1, and then overlaid with nutrient agarose in the form of a gel to ensure that there was no spread of virus throughout the culture. A range of concentrations of compound of known molarity was incorporated in the nutrient agarose overlay. Plaque numbers at each concentration were expressed as percentages of the control and a dose-response curve was drawn. From this curve the 50% inhibitory concentration ($IC_{50}$) was estimated.

| Compound | $IC_{50}$ μM |
|---|---|
| Example 1 | 3.8 |
| Acyclovir | 0.08–0.1 |

It should be appreciated that the compound of formula (I) may also exist in its tautomeric form

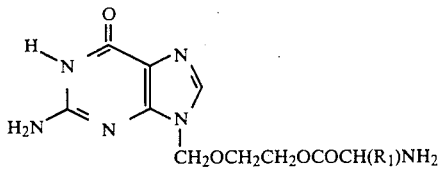

CH₂OCH₂CH₂OCOCH(R₁)NH₂ and both forms are intended to be included within the scope of the definition of formula (I) and the compounds according to the invention.

I claim:

1. The L form of a compound of formula (I)

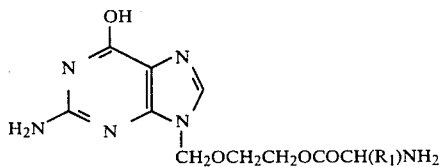

CH₂OCH₂CH₂OCOCH(R₁)NH₂ wherein R₁ represents a group of formula —CH[CH₃]CH₂CH₃ or a pharmaceutically acceptable salt thereof.

2. 2-(2-Amino-1,6-dihydro-6-oxo-9H(purin-9-yl)methoxy)ethyl L-isoleucinate.

3. A compound according to claim 1 which is 2-(2-amino-1,6-dihydro-6-oxo-9H(purin-9-yl)methoxy)ethyl L-isoleucinate.

4. A compound according to claim 1 which is 2-(2-amino-1,6-dihydro-6-oxo-9H(purin-9-yl)methoxy)ethyl L-isoleucinate hydrochloride.

5. A compound according to claim 1 which is in the form of a pharmaceutically acceptable salt.

6. A compound according to claim 5 wherein said salt is the hydrochloride salt.

7. A pharmaceutical composition comprising as active ingredient a compound of formula (I) as defined in claim 1 or a pharmaceutically acceptable salt thereof and a pharmaceutically acceptable carrier therefor.

8. A method of treating a susceptible viral infection in a mammal which comprises the administration to said mammal of an effective antiviral amount of a compound of formula (I) as defined in claim 1 or a pharmaceutically acceptable salt thereof.

9. The method of claim 8 wherein said viral infection is caused by a herpes virus.

10. A method of treating a herpes virus infection in a human having said infection which comprises orally or parenterally administering an effective herpes simplex virus infection treatment amount of 2-(2-amino-1,6-dihydro-6-oxo-9H(purin-9-yl)methoxy) ethyl-L-isoleucinate or a pharmaceutically acceptable salt thereof to said human.

11. The method of claim 10 in which the virus infection is a herpes simplex infection.

12. The method of claim 10 in which the virus infection is a herpes zoster infection.

13. The method of claim 10 in which the virus infection is a cytomegalovirus infection.

14. A tablet or capsule containing the compound 2-(2-amino-1,6-dihydro-6-oxo-9H(purin-9-yl)methoxy) ethyl-L-isoleucinate or a pharmaceutically acceptable salt thereof.

15. A method of generating acyclovir in the plasma of a mammal, which comprises orally administering the compound 2-(2-amino-1,6-dihydro-6-oxo-9H(purin-9-yl)methoxy) ethyl-L-isoleucinate or a pharmaceutically acceptable salt thereof.

16. The method of claim 15, in which the salt is an acid addition salt, which is orally administered.

17. The method of claim 16, in which the salt is the hydrochloride salt.

18. The method of claim 15, in which the compound is orally administered.

* * * * *